US006652596B2

(12) United States Patent
Smith et al.

(10) Patent No.: US 6,652,596 B2
(45) Date of Patent: Nov. 25, 2003

(54) SUSPENSION AID FOR ABOVE-KNEE PROSTHESIS

(76) Inventors: Mark W.L. Smith, 9107 Hillview Dr., DeSoto, KS (US) 66018; Elcia H. Thompson, 3247 Oregan Rd., Ottawa, KS (US) 66067

( * ) Notice: Subject to any disclaimer, the term of this patent is extended or adjusted under 35 U.S.C. 154(b) by 119 days.

(21) Appl. No.: 09/782,697

(22) Filed: Feb. 13, 2001

(65) Prior Publication Data

US 2002/0111575 A1 Aug. 15, 2002

(51) Int. Cl.$^7$ .............................. A61F 2/78; A61F 5/00

(52) U.S. Cl. ............................ 623/32; 623/33; 602/23; 602/62; 2/22

(58) Field of Search ............................ 623/31, 32, 33, 623/34; 602/32, 33, 62, 63, 26, 23; 2/22, 24

(56) References Cited

U.S. PATENT DOCUMENTS

| | | | | | |
|---|---|---|---|---|---|
| 976,550 | A | | 11/1910 | Coddington | |
| 4,207,885 | A | * | 6/1980 | Hampton et al. | 602/76 |
| 4,644,946 | A | | 2/1987 | Cremona-Bonato | |
| 4,761,324 | A | * | 8/1988 | Rautenberg et al. | 428/198 |
| 4,790,855 | A | * | 12/1988 | Jolly | 623/32 |
| 5,359,732 | A | * | 11/1994 | Waldman et al. | 2/243.1 |
| 5,376,130 | A | | 12/1994 | Courtney | |
| 5,382,223 | A | | 1/1995 | Springs | |
| 5,383,893 | A | | 1/1995 | Daneshvar | |
| 5,425,702 | A | * | 6/1995 | Carn et al. | 602/1 |
| 5,593,454 | A | * | 1/1997 | Helmy | 2/22 |
| 5,689,836 | A | * | 11/1997 | Fee et al. | 2/22 |
| 5,865,776 | A | * | 2/1999 | Springs | 602/26 |
| 6,059,834 | A | * | 5/2000 | Springs | 602/63 |

OTHER PUBLICATIONS

Syncor Ltd. packaging insert for “TES belt” (publication date unknown).

Jim Smith Sales, Inc. sales brochure entitled “Tri–Flex” (publication date unknown).

* cited by examiner

*Primary Examiner*—Danton D. DeMille
*Assistant Examiner*—Quang D Thanh
(74) *Attorney, Agent, or Firm*—Hovey Williams LLP

(57) ABSTRACT

A suspension aid for appending an above-knee prosthesis to a human body. The suspension aid is integrally formed of a resilient fabric having a warp knit leno, or equivalent, construction. The belt portion of the suspension aid extends substantially horizontally around the intertrochanteric region of the pelvis.

32 Claims, 4 Drawing Sheets

FIG. 4
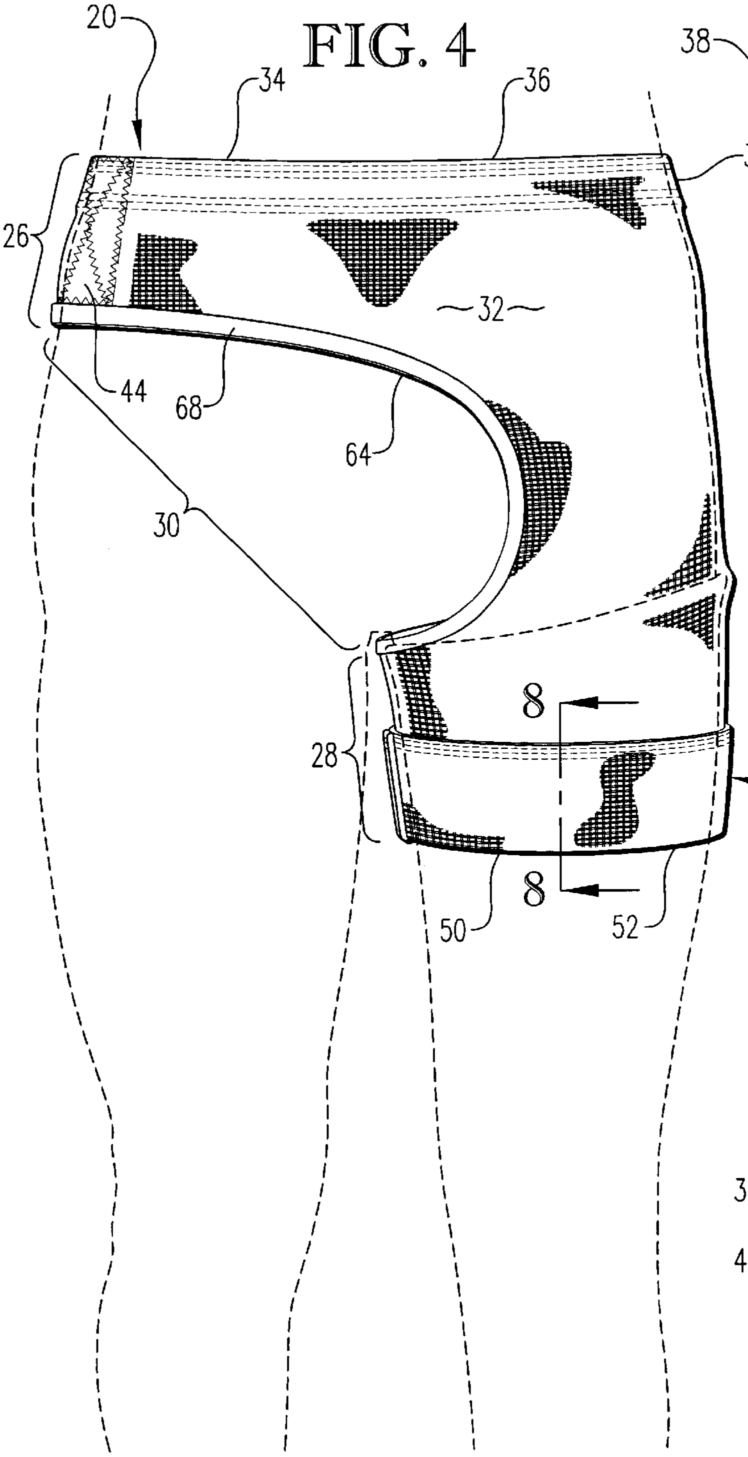
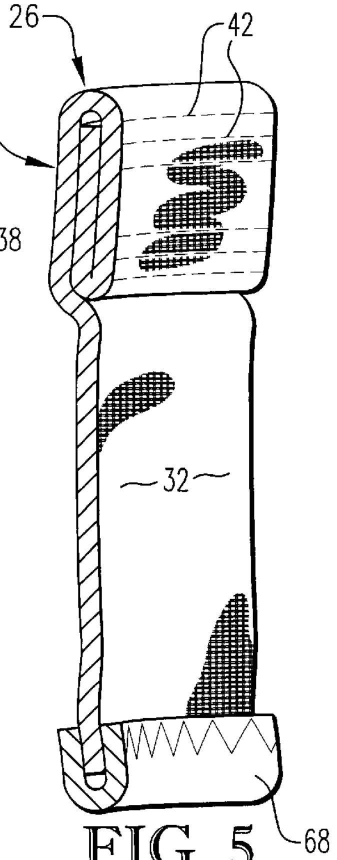
FIG. 5
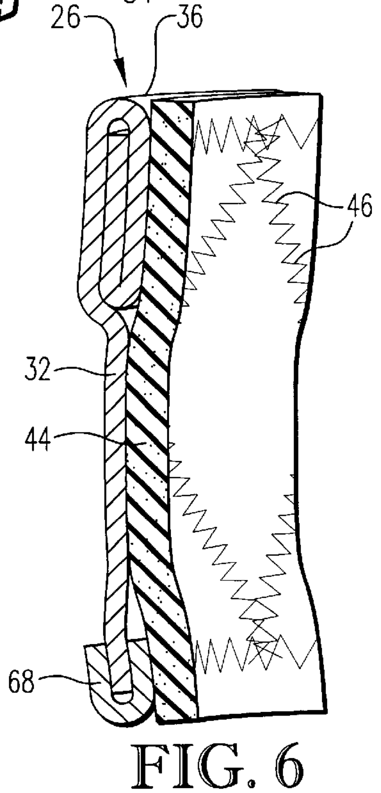
FIG. 6

SUSPENSION AID FOR ABOVE-KNEE PROSTHESIS

BACKGROUND OF THE INVENTION

1. Field of the Invention

The present invention relates generally to devices for attaching prosthetic limbs to the human body. More specifically, the present invention concerns a suspension aid for appending an above-knee prosthetic leg to a human body.

2. Discussion of Prior Art

In recent years many advances have been made in the field of prosthetics. For example, in the area of above-knee prosthetics, technology has been developed which allows the above-knee prosthetic device to closely mimic the performance and appearance of a natural leg. However, although numerous advances in the design of prosthetic devices have been made, there has not been a corresponding advance in systems for coupling prosthetic devices to the human body.

Many past suspension aids for coupling above-knee prosthetic legs to the human body were uncomfortable because they were constructed of rigid material which would not adequately stretch to conform to different body sizes or positions. Further, even those past suspension devices made of an elastic material were uncomfortable because the elastic material did not provide sufficient ventilation to allow body heat and sweat to pass therethrough.

In addition, many individuals who used past suspension aids considered them cosmetically unattractive because past suspension aids employed a number of mechanical attachment and adjustment devices such as, for example, belts, straps, harnesses, loops, and/or pulleys. These mechanisms added to the thickness and irregular shape of the suspension aid. Therefore, the waist, hips, buttocks, and/or thighs of the individual wearing past suspension aids had an irregular shape.

These various mechanical attachment and adjustment devices employed on past suspension aids added to the inconvenience of attaching and removing the prosthetic devices. The mechanical devices employed on past suspension aids also added to the expense of the suspension aid because manufacture was complex. Additionally, because of the location of the mechanical devices, many past suspension aids were not reversible, therefore, manufacture was more expensive because right-leg and left-leg suspension aids required separate construction.

SUMMARY OF THE INVENTION

In accordance with one embodiment of the present invention an apparatus for appending a prosthesis to a human body is provided. The apparatus comprises a first portion adapted to be secured to a human body and a second portion adapted to be secured to the prosthesis. The first portion and second portion comprise a warp knit leno fabric.

In accordance with another embodiment of the present invention an apparatus for appending a prosthesis to a human body is provided. The apparatus comprises a first portion adapted to be secured to the human body and a second portion adapted to be secured to the prosthesis. The first portion and second portion comprise a resilient fabric having a stretch in a first direction of from about 50 to about 200 percent at thirty pounds tension and a stretch in a second direction of from about 5 to about 100 percent at thirty pounds tension.

In accordance with a further embodiment of the present invention an apparatus for appending a prosthesis to a human body is provided. The apparatus comprises a first portion adapted to be secured to the human body and a second portion adapted to be secured to the prosthesis. The first portion has a continuous belt portion dimensioned to extend around the human body.

In accordance with a still further embodiment of the present invention an apparatus for appending a prosthesis to a human body is provided. The apparatus comprises a first portion adapted to be secured to the human body and a second portion adapted to be secured to the prosthesis. The second portion presents a prosthesis-receiving opening. The second portion includes a relatively inelastic adjustable closure for adjusting the size of the prosthesis-receiving opening.

The integral design of the present invention eliminates many of the mechanical attachment and adjustment devices required by some past suspension aids, thereby allowing for inexpensive manufacture, a more cosmetically pleasing appearance, a more comfortable fit, and/or more convenient attachment and removal. The symmetric design of one embodiment of the present invention makes it reversible and, therefore, less expensive to manufacture and distribute. The fabric of the present invention is thin and breathable so as to provide a cosmetically pleasing appearance and a more comfortable fit. Further, the fabric of the present invention stretches differently in different directions, thereby providing optimum prosthesis support with maximum human comfort.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein:

FIG. 4 is an elevation view showing the back of a suspension aid;

FIG. 5 is a sectional view taken along lines 5—5 in FIG. 2;

FIG. 6 is a sectional view taken along lines 6—6 in FIG. 2;

DETAILED DESCRIPTION OF THE PREFERRED EMBODIMENTS

Figure 1:
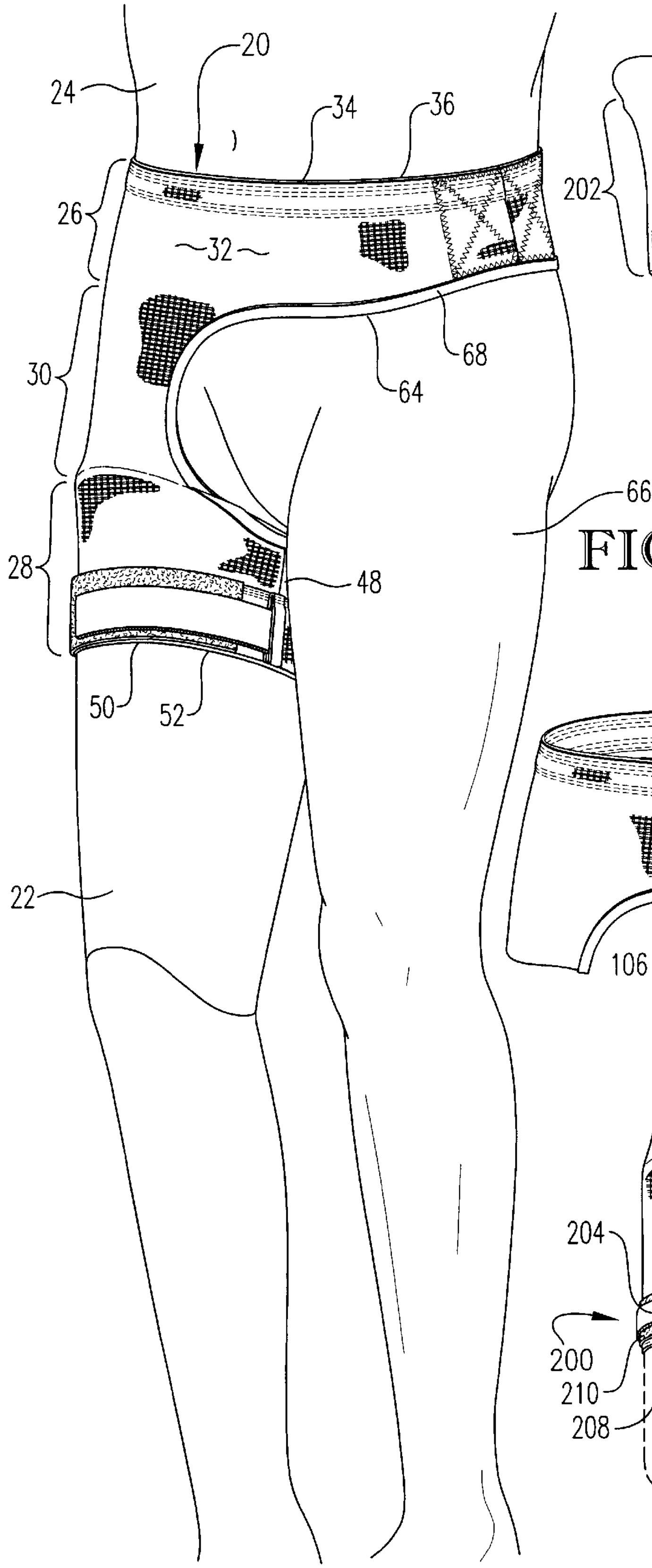
FIG. 1 is an elevation view showing the front of a suspension aid securing a prosthesis to a human body.

Turning initially to FIG. 1, the suspension aid 20 selected for illustration is designed to append a prosthesis 22 to a human body 24. Suspension aid 20 generally comprises a belt portion 26 for coupling suspension aid 20 to human body 24, a prosthesis coupling portion 28 for coupling suspension aid 20 to prosthesis 22, and a transition portion 30 for connecting belt portion 26 and prosthesis coupling portion 28. Belt portion 26, prosthesis coupling portion 28, and transition portion 30 are integrally formed of a fabric 32.

Fabric 32 is a resilient fabric. Preferably, fabric 32 has a warp stretch at thirty pounds tension of from about 50 to about 200 percent and a side stretch at thirty pounds tension of from about 10 to about 100 percent. More preferably, fabric 32 has a warp stretch of from about 90 to about 140 percent and a side stretch of from about 20 to about 50 percent at thirty pounds tension. Most preferably, fabric 32 has a warp stretch of from 110 to 120 percent and a side stretch of from 30 to 40 percent at thirty pounds tension. The warp direction of fabric 32 is substantially horizontal when human body 34 is erect, as shown in FIG. 1. To put it another way, the warp direction of fabric 32 is substantially parallel to the lengthwise orientation of belt portion 26. The side direction of fabric 32 is substantially vertical when human body 24 is erect, as shown in FIG. 1. To put it another way, the side direction of fabric 32 is substantially perpendicular to the lengthwise orientation of belt portion 26. The different directional elasticities of fabric 32 allows suspension aid 20 to securely couple prosthesis 22 to human body 24 without causing discomfort to human body 24.

Fabric 32 comprises nylon and spandex fibers. Preferably, fabric 32 comprises from about 40 to about 90 percent nylon fabrics and from about 3 to about 30 percent spandex fibers. More preferably, fabric 32 comprises from about 60 to about 75 percent nylon fibers and from about 20 to about 40 percent spandex fibers. Most preferably, fabric 32 comprises from 65 to 70 percent nylon fibers and from 25 to 35 percent spandex fibers. The nylon fibers of the fabric 32 preferably have a weight from about 30 to about 300 denier, most preferably from 90 to 120 denier. The spandex fibers of fabric 32 preferably have a weight from about 200 to about 3000 denier, most preferably from 700 to 1000 denier. This mix of nylon and spandex fibers permits suspension aid 20 to be sufficiently elastic while still exhibiting sufficient durability.

The weight of fabric 32 is preferably from about 3 to about 30 ounces per square yard, more preferably from about 7 to about 12 ounces square yard, most preferably from 9 to 10 ounces per square yard. The thickness of fabric 32 is preferably less than ⅛ inch, most preferably less than 1/16 inch.

Fabric 32 is a relatively open fabric which allows heat and sweat to escape from human body 24. As used herein, the term "openness" refers to the percentage of the surface area of an unstretched fabric which is completely open. Openness of a fabric can be determined by directing a beam of visible light at the fabric, perpendicular to the surface of the fabric. The percentage of undeflected light which passes directly through the fabric, perpendicular to the fabric surface, is a measure of the openness of the fabric. Fabric 32 preferably has an openness of more than about 2 percent, more preferably more than about 5 percent, and most preferably more than 10 percent.

Fabric 32 is preferably a warp knit fabric having the above-described properties. More preferably, fabric 32 is a warp knit leno fabric having the above-described properties. Suitable warp knit leno fabrics include, for example, Darlington #1252 Leno, manufactured by Darlington Fabrics Corporation, New York, N.Y.

With reference to FIGS. 1–8, the configuration of suspension aid 20 will now be described in greater detail. As shown in FIG. 1, belt portion 26 comprises a unitary piece of fabric 32 which extends in a continuous fashion around human body 24. Belt portion 26 defines a body-receiving opening 34 which, due to the resilient construction of belt portion 26, is adjustable to different body sizes and position. Because belt portion 26 comprises a unitary piece of fabric 32, fabric 32 must be deformed in order to adjust the size of body-receiving opening 34.

Belt portion 26 has an upper end which defines an upper terminal end 36 of suspension aid 20 and a lower end connected to transition portion 30. Upper terminal end 36 of suspension aid 20 is preferably maintained in substantially horizontal orientation when human body 24 is in an erect position, as shown in FIG. 1. Further, upper terminal end 36 is preferably maintained in a position substantially below the ilium of human body 24. The horizontal configuration of belt portion 26 below the ilium more evenly distributes compressive forces on body 24. Further, the configuration of belt 26 distributes the prosthesis appending forces about the intertrochanteric region of the pelvis of the human body 24, thereby adding to the comfort and efficacy of suspension aid 20 versus prior art devices which extended at an angle above the ilium on the side opposite the prosthesis.

Figure 2:
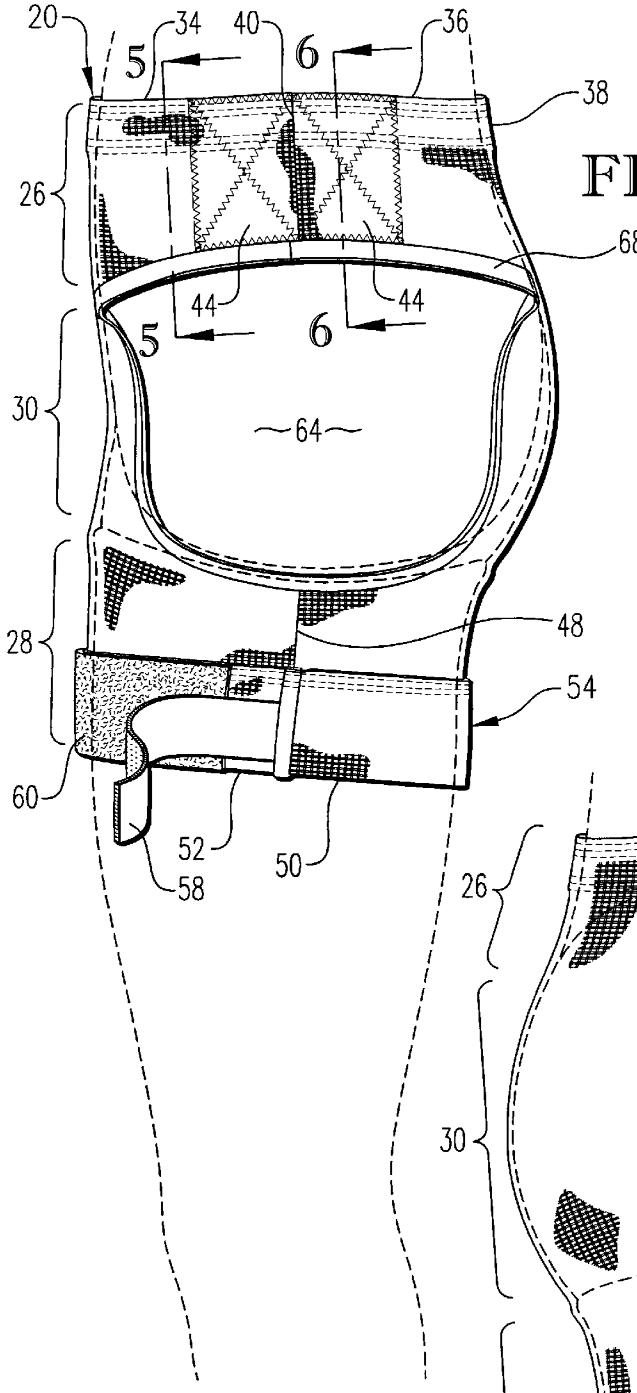
FIG. 2 is an elevation view showing the inner-thigh side of a suspension aid.
Figure 3:
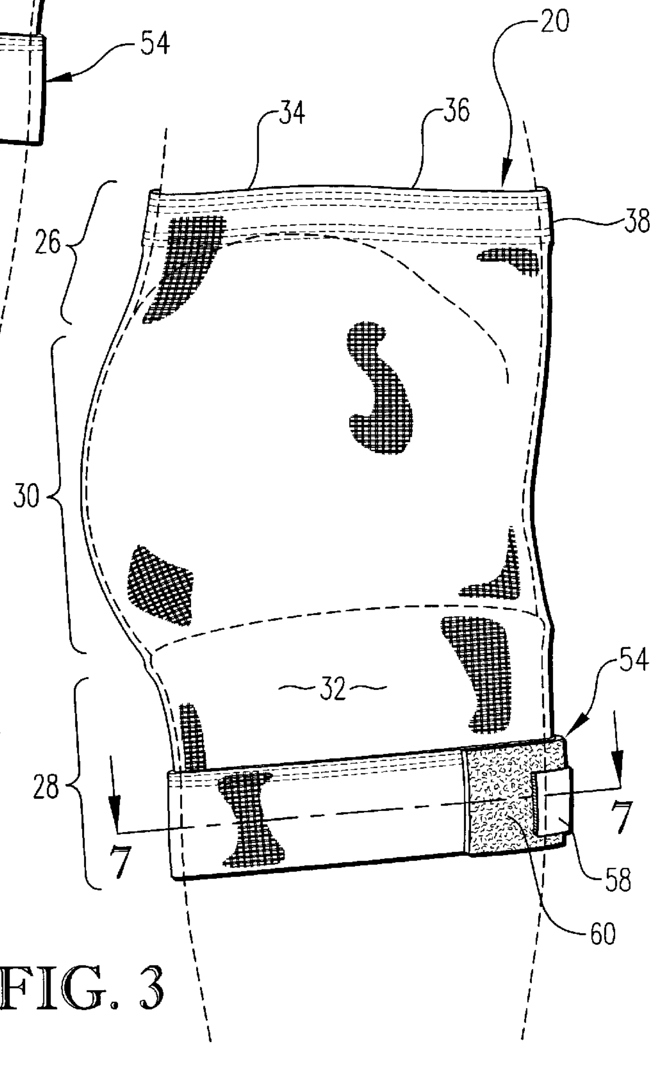
FIG. 3 is an elevation view showing the outer-thigh side of a suspension aid.

As perhaps best seen in FIGS. 2,5 and 6, belt portion 26 includes a waist band 38 and a single permanent belt seam 40. The top of waistband 38 defines upper terminal end 36 of suspension aid 20. As seen in FIG. 5, waistband 38 can be formed of multiple layers of fabric 32 sewn together by expandable stitching 42. Therefore, waistband 38 is less elastic than fabric 32 because its resistance to stretching is compounded with layer of fabric 32. As best seen in FIG. 2, seam 40 permanently connects the two ends of fabric 32. Seam 40 can be strengthened by reinforcement 44 extending on each side of seam 40 and permanently attached to fabric 32 and waistband 38 by stitching 46, shown in FIG. 6. Alternatively, any type of expandable hem known in the art can be employed as an alternative to waistband 38.

Referring again to FIG. 1, prosthesis coupling portion 28 comprises a unitary piece of fabric 32 which extends in a continuous fashion around prosthesis 22. The two ends of fabric 32 of prosthesis coupling portion 28 are connected by a permanent seam 48. Prosthesis coupling portion 28 defines a prosthesis-receiving opening 50 which is adjustable due to the resilience of fabric 32 and sized to exert an inward holding force on prosthesis 22. Prosthesis coupling portion 28 has a lower end which defines a lower terminal end 52 of suspension aid 20 and an upper end integral with transition portion 30.

Figure 8:
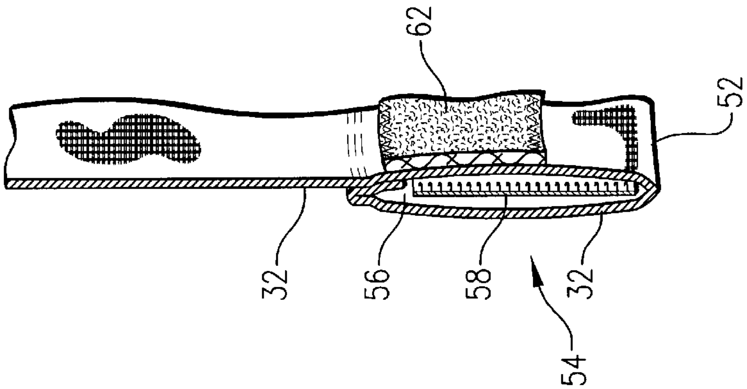
FIG. 8 is a sectional view taken along lines 8—8 in FIG. 4.
Figure 7:
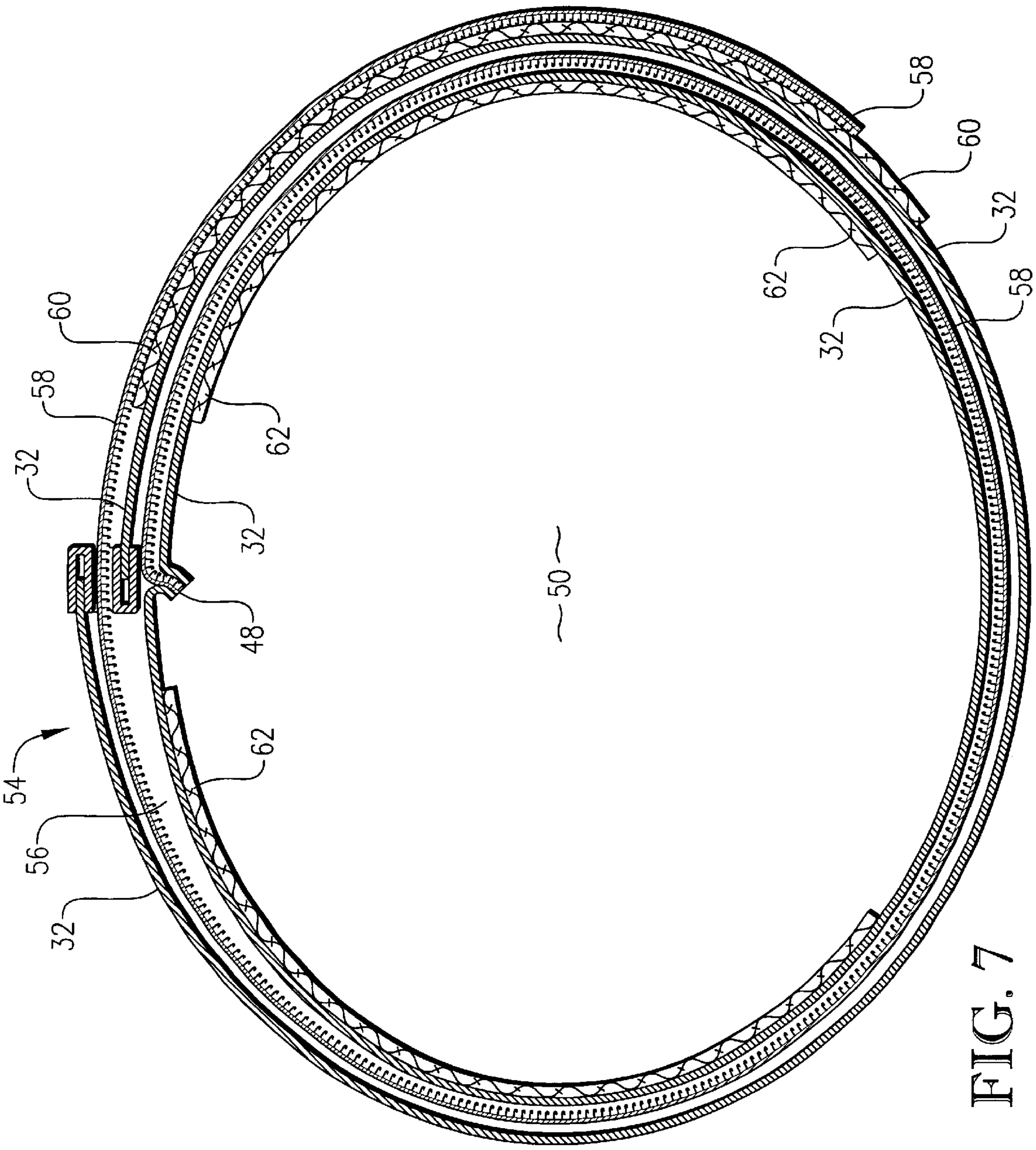
FIG. 7 is a sectional view taken along lines 7—7 in FIG. 3.

As perhaps best illustrated in FIGS. 2, 3, 7, and 8, prosthesis coupling portion 28 can include an adjustable closure 54. As best seen in FIGS. 7 and 8, adjustable closure 54 generally includes a circumferential channel 56 for receiving a strap 58. As best seen in FIG. 8, channel 56 is formed by folding a downwardly extending portion of fabric 32 upward at terminal end 52 and attaching the upwardly folded portion of fabric 32 to the downwardly extending portion of fabric 32 above terminal end 52. This creates circumferential channel 56 between the downwardly extending fabric 32 and the upwardly folded fabric 32.

Referring again to FIGS. 2 and 7, strap 58 generally has a first end which is secured to fabric 32 at prosthesis coupling seam 48, a middle portion which extends through channel 56, and a second end which can be releasably secured to a catch 60. Catch 60 is attached to the upwardly folded portion of fabric 32. The size of prosthesis-receiving opening 50 can be adjusted by varying the position of the second end of strap 50 relative to catch 60. Strap 58 is preferably a relatively inelastic material as compared to fabric 32. The relative inelasticity of strap 58 allows adjustable closure 54 to exert a consistent and substantial compressive holding force on the prosthetic device. The second end of strap 58 can be releasably secured to catch 60 by any means known in the art such as, for example, a hook-and-loop fastener. Adjustable closure 54 can include a layer of high friction material 62 disposed on the inside of prosthesis-receiving opening 50 for more securely coupling the prosthesis to suspension aid 20. Such high friction material can be, for example, a silicone surface coating.

Referring back to FIGS. 1 and 2, transition portion 30 has an upper end coupled to belt portion 26 and a lower end coupled to prosthesis coupling portion 28. Fabric 32 of belt portion 26, transition portion 30, and prosthesis coupling portion 28 is preferably a substantially symmetric, unitary piece of fabric 32, thereby enabling suspension aid 20 to distribute a comprehensive holding force over the entire surface area of the body 24 which contacts fabric 32. Fabric 32 of transition portion 30 conveys vertical and horizontal supporting forces between belt portion 26 and prosthesis coupling portion 28 to thereby restrict movement of prosthesis 22 relative to erect human body 24. Transition portion 30 presents a curvilinear natural leg opening 64 through which natural leg 66 can be extended when suspension aid 20 is coupled to human body 24. Natural leg opening 64 is dimensioned so as to prevent fabric 32 from covering the genital region of human body 24. As perhaps best seen in FIGS. 5 and 6, the outer edge of natural leg opening 64 includes a hem 68 to prevent fraying of fabric 32.

Figure 9:
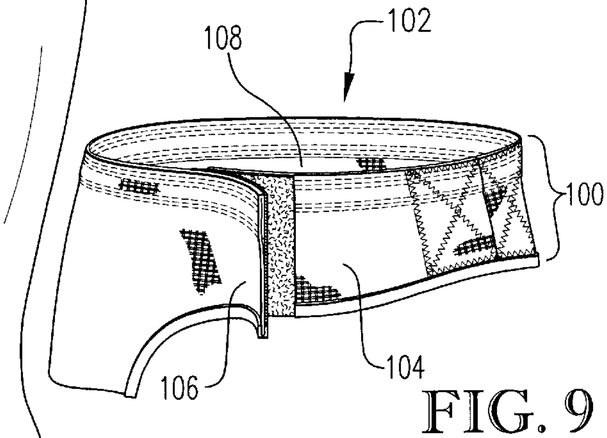
FIG. 9 is an elevation view showing the front upper portion of an alternative suspension aid.

FIG. 9 shows an alternate construction for a belt portion 100 of a suspension aid 102. In the illustrated embodiment, belt portion 100 has a first end 104 and a second end 106 which can be releasably secured to one another. The size of a body receiving opening 108 can be adjustable by varying the position of first end 104 relative to second end 106. First end 104 and second end 106 can be releasably secured using any means known in the art such as, for example, a hook-and-loop fastener. The configuration of belt portion 100 allows for suspension aid 102 to be quickly coupled and decoupled from a human body.

Figure 11:
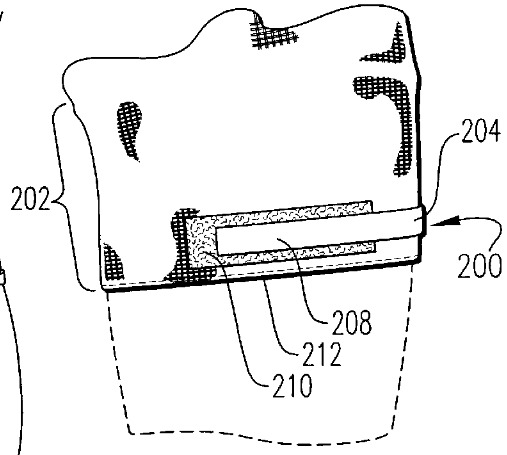
FIG. 11 is an elevation view showing the outer-thigh side of the lower portion of an alternative suspension aid.
Figure 10:
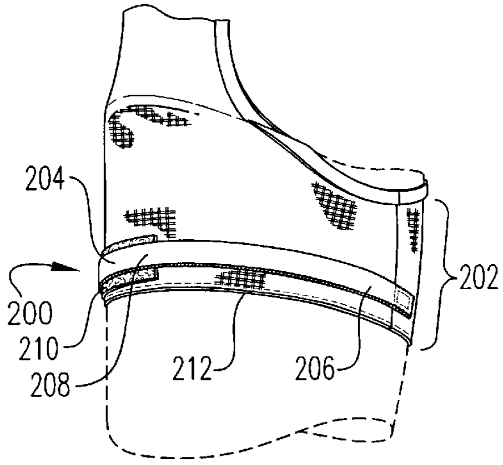
FIG. 10 is an elevation view showing the inner-thigh side of the lower portion of an alternative suspension aid.

FIGS. 10 and 11 show an alternate construction for an adjustable closure 200 of a prosthesis coupling portion 202 of a suspension aid. In this embodiment, a relatively inelastic strap 204 has a first end 206 coupled to the inner-thigh portion of prosthesis coupling portion 202 and a second end 208 releasably secured to a catch 210 which is coupled to the outer-thigh portion of prosthesis coupling portion 202. Second end 208 can be releasably secured to catch 210 by any means known in the art, such as, for example, a hook-and-loop attachment. Adjusting the position of second end 208 relative to catch 210 varies the size of prosthesis receiving opening 212 to thereby provide an adjustable inward securing force on the prosthetic device received in prosthetic-receiving opening 212.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. An apparatus for appending a prosthesis to a human body, said apparatus comprising:

a first portion adapted to be secured to the human body; and a second portion adapted to be secured to the prosthesis, said first and second portions comprising a warp knit leno fabric, said fabric having a stretch in a substantially horizontal direction of from about 50 to about 200 percent at 30 pounds tension and a stretch in a substantially vertical direction of from about5 to about 100 percent at 30 pounds tension when the apparatus is donned on the erect human body.

2. An apparatus as claimed in claim 1, said fabric comprising spandex fibers.

3. An apparatus as claimed in claim 1, said fabric comprising nylon fibers.

4. An apparatus as claimed in claim 1, said fabric comprising from about 10 to about 60 percent spandex fibers and from about 40 to about 90 percent nylon fibers.

5. An apparatus as claimed in claim 4, said fabric having a weight of from about 30 to about 30 ounces per square yard.

6. An apparatus as claimed in claim 5, said spandex fibers having a weight of from about 200 to about 3000 denier, said nylon fibers having a weight of from about 30 to about 300 denier.

7. An apparatus as claimed in claim 1, said fabric comprising from about 20 to about 40 percent spandex fibers and from about 60 to about 75 percent nylon fibers.

8. An apparatus as claimed in claim 7, said fabric having a stretch in the substantially horizontal direction of from about 70 to about 140 percent at 30 pounds tension and a stretch in the substantially vertical direction of from about 20 to about 50 percent at 30 pounds tension when the apparatus is donned on the erect human body.

9. An apparatus as claimed in claim 8, said fabric having a weight of from about 7 to about 12 ounces per square yard.

10. An apparatus as claimed in claim 9, said spandex fibers having a weight of from about 700 to about 1000 denier, said nylon fibers having a weight of from about 90 to about 110 denier.

11. An apparatus for appending a prosthesis to a human body, said apparatus comprising:

a first portion adapted to be secured to the human body; and a second portion adapted to be secured to the prosthesis, said first and second portions comprising a resilient fabric having a stretch in a first direction of from about 50 to about 200 percent at 30 pounds tension and a stretch in a second direction perpendicular to the first direction of from about 5 to about 100 percent at 30 pounds tensions, said first direction being substantially horizontal and said second direction being substantially vertical when the first portion is secured to the erect human body.

12. An apparatus as claimed in claim 11, said fabric having a weight of from about 30 to about 30 ounces per square yard.

13. An apparatus as claimed in claim 11, said fabric having an openness of more than about 2 percent.

14. An apparatus as claimed in claim 11, said fabric comprising nylon and spandex.

15. An apparatus as claimed in claim 11, said fabric having a stretch in the first direction of from about 90 to about 140 percent at 30 pounds tension and a stretch in the second direction of from about 20 to about 50 percent at 30 pounds tension.

16. An apparatus as claimed in claim 15, said fabric having a weight of from about 7 to about 12 ounce per square yard.

17. An apparatus as claimed in claim 15, said fabric having an openness of more than about 5 percent.

18. An apparatus as claimed in claim 15, said fabric comprising from about 20 to about 40 percent spandex fibers and from about 60 to about 75 percent nylon fibers.

19. An apparatus for appending a prosthesis to a human body, said apparatus comprising:

a first portion adapted to be secured to the human body, said first portion having an endless belt portion dimensioned to extend around the human body; and a second portion adapted to be secured to the prosthesis, said first and second portions comprising a resilient fabric, said belt portion defining a body-receiving opening, wherein the size of the body-receiving opening can only be increased by stretching the resilient fabric, said fabric having a stretch in a first direction of from about 50 to about 200 percent at 30 pounds tension and a stretch in a second direction of from about 5 to about 100 percent at 30 pounds tension, said apparatus adapted to be oriented relative to the human body so that the first direction of the fabric is substantially horizontal and the second direction of the fabric is substantially vertical when the human body is erect.

20. An apparatus as claimed in claim 19, said belt portion dimensioned to extend around the human body substantially below the ilium of the human body.

21. An apparatus as claimed in claim 20, said second portion adapted to be secured to a prosthetic leg.

22. An apparatus as claimed in claim 21, said fabric having a stretch in the first direction of from about 90 to about 140 percent at 30 pounds tension and a stretch in the second direction of from about 20 to about 50 percent at 30 pounds tension.

23. An apparatus as claimed in claim 22, said fabric having a weight of from about 7 to about 12 ounces per square yard.

24. An apparatus as claimed in claim 23, said fabric having an openness of more than about 5 percent.

25. An apparatus as claimed in claim 24, said fabric comprising from about 20 to about 40 percent spandex fibers and from about 60 to about 75 percent nylon fibers.

26. An apparatus as claimed in claim 25, said belt portion configured to extend substantially horizontally around the erect human body.

27. An apparatus as claimed in claim 26, said belt portion configured to be worn substantially around the intertrochanteric region of the erect human body.

28. An apparatus as claimed in claim 19, said first portion and said second portion integrally formed of the resilient fabric.

29. An apparatus for appending a prosthesis to a human body, said apparatus comprising:

a belt portion adapted to be secured around the torso of the human body; and a prosthesis coupling portion adapted to be secured to the prosthesis, said belt portion presenting an upper terminal edge, said upper terminal edge being substantially straight so that when the apparatus is donned on the human body the upper terminal edge extends around the erect human body in a substantially horizontal fashion, said belt portion and said prosthesis coupling portion being formed of a resilient fabric having a stretch in a substantially horizontal direction of from about 50 to about 200 percent at 30 pounds tension and a stretch in a substantially vertical direction of from about 5 to about 100 percent at 30 pounds tension when the apparatus is donned on the erect human body.

30. An apparatus as claimed in claim 29, said belt portion being configured so that the upper terminal edge is positioned below the ilium of the human body when the apparatus is donned on the erect human body.

31. An apparatus as claimed in claim 30, said belt portion being configured so that the upper terminal edge extends around the intertrochanteric region of the human body when the apparatus is donned on the erect human body.

32. An apparatus as claimed in claim 29, said belt portion and said prosthesis coupling portion comprising a common piece of warp knit leno fabric.

* * * * *